United States Patent
Jezek et al.

(10) Patent No.: US 11,291,725 B2
(45) Date of Patent: Apr. 5, 2022

(54) LIQUID PHARMACEUTICAL COMPOSITION

(71) Applicant: FRESENIUS KABI DEUTSCHLAND GMBH, Bad Homburg (DE)

(72) Inventors: Jan Jezek, Saffron Walden (GB); Luca Badiali, Cambridge (GB); David Gerring, Cambridge (GB)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 42 days.

(21) Appl. No.: 16/346,215

(22) PCT Filed: Oct. 30, 2017

(86) PCT No.: PCT/EP2017/077793
§ 371 (c)(1),
(2) Date: Apr. 30, 2019

(87) PCT Pub. No.: WO2018/078162
PCT Pub. Date: May 3, 2018

(65) Prior Publication Data
US 2019/0262450 A1    Aug. 29, 2019

(30) Foreign Application Priority Data
Oct. 31, 2016   (EP) .................................. 16196625

(51) Int. Cl.
| | |
|---|---|
| *A61K 39/395* | (2006.01) |
| *A61K 47/02* | (2006.01) |
| *A61K 47/12* | (2006.01) |
| *A61K 47/18* | (2017.01) |
| *A61K 47/20* | (2006.01) |
| *A61K 47/22* | (2006.01) |
| *A61K 47/26* | (2006.01) |
| *C07K 16/28* | (2006.01) |
| *A61K 9/08* | (2006.01) |
| *A61P 37/00* | (2006.01) |
| *A61K 9/00* | (2006.01) |

(52) U.S. Cl.
CPC ...... *A61K 39/39591* (2013.01); *A61K 9/0019* (2013.01); *A61K 9/08* (2013.01); *A61K 47/02* (2013.01); *A61K 47/12* (2013.01); *A61K 47/183* (2013.01); *A61K 47/20* (2013.01); *A61K 47/22* (2013.01); *A61K 47/26* (2013.01); *A61P 37/00* (2018.01); *C07K 16/2866* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 8,562,967 B2 * | 10/2013 | Hinderer | A61P 7/00 424/85.1 |
| 9,539,263 B2 * | 1/2017 | Zhang | A61K 9/0019 |
| 2012/0301460 A1 * | 11/2012 | Bao | A61K 38/47 424/133.1 |
| 2015/0071879 A1 * | 3/2015 | Jezek | A61K 38/27 424/85.6 |
| 2015/0150979 A1 * | 6/2015 | Yates | A61K 39/39591 424/133.1 |

FOREIGN PATENT DOCUMENTS

JP    2009034095 A    2/2009

OTHER PUBLICATIONS

Wang et al., J Pharm Sci 96(1): 1-26, 2007; abstract; p. 5, col. 1; pp. 8-14. (Year: 2007).*
Wang et al.,(2000) Int J Pharmaceutics 203: 1-60 (Year: 2000).*
Carpenter et al. (1997), (Pharm Res 14(8): 969-975, 1997) (Year: 1997).*
Fukuda et al. Pharm Res 31: 992-1001, 2014; (Year: 2014).*
Kim et al. Int J Pharmaceutics 51: 26-37, (2016) (Year: 2013).*

* cited by examiner

*Primary Examiner* — Gary B Nickol
*Assistant Examiner* — Jegatheesan Seharaseyon
(74) *Attorney, Agent, or Firm* — James S. Keddie; Bozicevic, Field & Francis LLP

(57) ABSTRACT

The present invention relates to a novel protein formulation. In particular, the invention relates to a liquid pharmaceutical composition of tocilizumab, a method of manufacturing the composition, a kit including the composition, a package including the composition and to methods of treatment using the composition and/or package.

18 Claims, No Drawings
Specification includes a Sequence Listing.

LIQUID PHARMACEUTICAL COMPOSITION

CROSS-REFERENCE TO RELATED APPLICATIONS

This application is a § 371 national phase of International Application No. PCT/EP2017/077793, filed on Oct. 30, 2017, which claims the benefit of European Application No. 16196625.4, filed on Oct. 31, 2016, which applications are incorporated by reference herein.

INTRODUCTION

The present invention relates to a novel protein formulation. In particular, the invention relates to a liquid pharmaceutical composition of tocilizumab, a method of manufacturing the composition, a kit including the composition, a package including the composition and methods of treatment using the composition and/or package.

BACKGROUND

Several biologics have been approved since the 90's for treating autoimmune diseases, such as rheumatoid arthritis, juvenile arthritis and other autoimmune diseases. Among others, there are drugs targeting Tumor Necrosis Factor-α (such as Etanercept (marketed as Enbrel®), Adalimumab (marketed as Humira®) or Infliximab (marketed as Remicade®) as well as Interleukin-6 receptor (IL-6R) (such as tocilizumab (marketed as ROACTEMRA® or Actemra®)). Other drugs targeting IL-6R for the treatment of these disorders are under development or already in pre-registration before the health authorities, such as sapelizumab, vobarilizumab or sarilumab.

Tocilizumab for instance is generally delivered to a patient either via intravenous injection or subcutaneous injection, and is provided in a liquid form, typically in packages such as vials, pre-filled syringes, or pre-filled pen devices. Commercial formulations (ACTEMRA®) of tocilizumab comprise the following ingredients:

| Ingredients of the intravenous formulation | Ingredients of the subcutaneous formulation |
| --- | --- |
| Tocilizumab (20 mg/mL) | Tocilizumab (180 mg/mL) |
| disodium phosphate dodecahydrate | polysorbate 80 |
| sodium dihydrogen phosphate dehydrate | L-histidine and L-histidine monohydrochloride |
| polysorbate 80 | L-arginine and L-arginine hydrochloride |
| sucrose | L-methionine |
| water for injection | water for injection |
| pH of about 6.5 | pH of about 6.0 |

These formulations have been described respectively in PCT applications WO03/068260 and WO2009/084659. Other formulations directed to anti-IL-6R antibodies have been described such as the ones in WO02/13860, WO2011/085158 or yet WO2013/063510.

When preparing a pharmaceutical composition comprising a bioactive protein, such as an antibody, said composition must be formulated in such a way that the activity of the protein is maintained for an appropriate period of time. A loss in activity/stability of the protein may result from chemical or physical instabilities of the protein notably due to denaturation, aggregation or oxidation. The resulting products may thus be pharmaceutically unacceptable, especially after storage for a long time. Although the use of excipient(s) is known to increase the stability of a given protein, the stabilizing effects of these excipients is highly dependent of the nature of the excipients and of the bioactive protein itself.

As underlined with tocilizumab, generally the antibodies are formulated with different excipients when they are marketed with different strengths (e.g. 20 mg/mL versus 180 mg/mL) or with different presentations (e.g. intravenous versus subcutaneous).

There remains a need for further formulations containing tocilizumab, as an active ingredient, wherein said formulations are stable for an appropriate period of time and suitable for use in injection, preferably for any type of injections. Said formulations could be useful for administration in the treatment of autoimmune diseases, such as rheumatoid arthritis and juvenile idiopathic arthritis. Even if the overall performance of the commercial formulations could not be surpassed, an alternative formulation having comparative performance but being useful whatever the concentration of the antibody or whatever its presentation would represent a highly desirable replacement for the commercial formulations. Desirably, the problem(s) of the prior art may be solved whilst reducing the complexity of the formulation(s).

SUMMARY OF THE INVENTION

According to a first aspect of the present invention here is provided a liquid pharmaceutical composition comprising tocilizumab (an anti-IL-6R antibody), a histidine buffer and a stabilizer selected from lactic acid or salts thereof. Said composition further comprises a free amino acid, a surfactant and optionally a salt. Said composition is (substantially or entirely) free of methionine (suitably L-methionine).

According to a second aspect of the present invention there is provided a method of manufacturing a liquid pharmaceutical composition, the method comprising mixing together tocilizumab, a histidine buffer and a stabilizer selected from lactic acid or salts thereof, a free amino acid, a surfactant and optionally a salt. Also provided is a liquid pharmaceutical composition obtainable by, obtained by, or directly obtained by a method of manufacturing a liquid pharmaceutical composition as defined herein.

According to a third aspect of the present invention there is provided a drug delivery device (e.g. pre-filled syringe or pen, or intravenous bag) comprising a liquid pharmaceutical composition as defined herein.

According to a fourth aspect of the present invention, here is provided a kit of parts comprising a drug delivery device, a liquid pharmaceutical composition as defined herein (optionally contained in a package or container), and optionally a set of instructions with directions regarding the administration (e.g. intravenous or subcutaneous) of the liquid pharmaceutical composition.

In a fifth aspect of the present invention, here is described a package (e.g. pre-filled syringe, pen, intravenous bag, or a package/container containing any of the aforementioned) comprising a liquid pharmaceutical composition as defined herein.

According to a sixth aspect of the present invention, here is provided a method of manufacturing a package or a drug delivery device, the method comprising incorporating a liquid pharmaceutical composition as defined herein within a package or drug delivery device. Also provided is a package or a drug delivery device obtainable by, obtained by, or directly obtained by a method of manufacturing a package or a drug delivery device as defined herein.

According to a seventh aspect of the present invention, here is described a liquid pharmaceutical composition as defined herein for use in therapy.

Definitions

Any features, including optional, suitable, and preferred features, described in relation to any particular aspect of the invention may also be features, including optional, suitable and preferred features, of any other aspect of the present invention.

Unless otherwise stated, the following terms used in the specification and claims have the following meanings set out below.

The term "antibody", and its plural form "antibodies", as used herein includes, inter alia, polyclonal antibodies, affinity-purified polyclonal antibodies, monoclonal antibodies, and antigen-binding fragments, such as nanobodies, F(ab')2, Fab proteolytic fragments, and single chain variable region fragments (scFvs). It refers both to one-armed (monovalent) or two-armed (bivalent) antibody.

The term "recombinant antibody" is intended to include an antibody prepared, expressed, produced or isolated using a recombinant method.

The term "anti-IL-6R antibody" refers to an antibody directed to Interleukin-6 receptor (i.e. IL-6R). Preferably, it is an antibody which does not only bind to its target, i.e. the IL-6R, but also neutralize it (alternatively inhibit it or antagonize it).

The term "tocilizumab" include the originator active pharmaceutical ingredient (as commercially available under the trade names Actemra® or RoActemra®), as defined in WO9219759 (particularly hPM-1 therein) and elsewhere in the art, and also biosimilars thereof. Tocilizumab has a light chain variable region (LCVR) comprising the amino acid sequence of SEQ ID NO: 1 and a heavy chain variable region (HCVR) comprising the amino acid sequence of SEQ ID NO: 2. It has a molecular weight of about 145 kDa.

The term "biosimilar" refers to a drug substance which share full protein sequence identity with a given active pharmaceutical ingredient (i.e. approved by health Authorities). It is noted that a biosimilar may have a (slightly) different glycosylation profile, even if the protein sequence is substantially the same or different to the extent specified above. Such "biosimilars" would need to be officially approved as a "biosimilar" for marketing before said "biosimilar" is sold on the market. The term "buffer", as used herein, refers to solutions of compounds that are known to be safe in formulations for pharmaceutical or veterinary use and that have the effect of maintaining or controlling the pH of the formulation in the pH range desired for the formulation. Acceptable buffers for controlling pH at a moderately acidic pH to a moderately basic pH include, but are not limited to, phosphate, acetate, citrate, TRIS, and histidine, salts and/or acidic forms thereof, and/or any combination thereof. "TRIS" refers to 2-amino-2-hydroxymethyl-1,3,-propanediol, and to any pharmacologically acceptable salt thereof. The preferred buffer according to the invention is histidine buffer.

The compound(s) making the buffer are also called "buffering agent(s)". The pH of a buffer will change only slightly upon addition of a small quantity of strong acid or base due to the buffering effect imparted by the buffering agent. It is noted that a given concentration of a histidine buffer for instance generally relates to the combined concentration of the conjugate base form of histidine (i.e. unprotonated imidazole form) and the conjugate acid form of histidine (i.e. and the protonated imidazolium form; or histidine salt). Such concentrations are usually straightforward to calculate by reference to the input quantities of histidine or a salt thereof. The overall pH of the composition is generally a reflection of the equilibrium concentration of each of the relevant buffering species (i.e. the balance of buffering agent(s) to acid/base conjugate(s) thereof).

Herein, the term "buffering agent" refers to an acid or base component (usually a weak acid or weak base) of a buffer or buffer solution. A buffering agent helps maintain the pH of a given solution at or near to a pre-determined value, and the buffering agents are generally chosen to complement the pre-determined value. A buffering agent is suitably a single compound which gives rise to a desired buffering effect, especially when said buffering agent is mixed with (and suitably capable of proton exchange with) an appropriate amount (depending on the pre-determined pH desired) of its corresponding acid/base conjugate, or if the required amount of its corresponding acid/base conjugate is formed in situ—this may be achieved by adding strong acid or base until the required pH is reached.

Unless stated otherwise, references herein to an "amino acid" or "amino acids", whether specific (e.g. arginine, histidine) or general (e.g. any amino acid), in the context of their presence or otherwise within compositions (especially pharmaceutical liquid compositions of the invention) relate to the corresponding free amino acid(s) (regardless of its/their protonation state and/or salt form, though for consistency amounts are suitably calculated by reference to the free amino acid per se). This may suitably include natural and/or artificial amino acids. Unless stated to the contrary, such references are not intended to relate to amino acid residue(s) covalently incorporated as part of a larger compound (as opposed to a composition comprising multiple compounds), such as a peptide or protein (where such amino acid residues are linked via peptide bonds). As such, for example, though tocilizumab, as a protein, contains amino acid residues, it is not considered to comprise any "free amino acid(s)". By way of example, a composition defined as being "free of methionine" does not contain any free methionine but it may still include one or more proteins (e.g. tocilizumab) which do themselves comprise methionine residues. Unless stated otherwise, references herein to any one or more "amino acids", whether specific or general, suitably relate to the L-stereoisomers or a racemate thereof, most suitably L-amino acids. Depending on its properties, said free amino acid can be a stabilizer.

The term "substantially free", when used in relation to a given component of a composition (e.g. "a liquid pharmaceutical composition substantially free of methionine"), refers to a composition to which essentially none of said component has been added. As explained above, such references have no bearing on the presence of amino acid residue(s) within a protein structure. When a composition is "substantially free" of a given component, said composition suitably comprises no more than 0.001 wt % of said component, suitably no more than 0.0001 wt % of said component, suitably no more than 0.00001 wt %, more suitably no more than 0.000001 wt.

The term "entirely free", when used in relation to a given component of a composition (e.g. "a liquid pharmaceutical composition entirely free of methionine"), refers to a composition containing none of said component. As explained above, such references have no bearing on the presence of amino acid residue(s) within a protein structure.

The term "stability", as used herein, refers to the physical, chemical, and conformational stability of tocilizumab in the formulations according to the present invention (and including maintenance of biological potency). Instability of a protein formulation may be caused by chemical degradation or aggregation of the protein molecules to form higher order polymers, deglycosylation, modification of glycosylation, oxidation or any other structural modification that reduces at least one biological activity of an antibody of the present invention.

The term "stable" solution or formulation, as used herein, is one solution or formulation wherein the degree of degradation, modification, aggregation, loss of biological activity and the like, of proteins therein is acceptably controlled, and does not increase unacceptably with time. It thus generally refers to the physical stability and/or chemical stability and/or biological stability of a component, typically an active or composition thereof, during preservation/storage. Preferably, the formulation retains at least more than 80% of the antibody activity over a period of at least 12 months at 2-8° C. for instance. The stabilized antibody formulation of the present invention has preferably a shelf-life of at least about 12 months, 18 months, more preferably at least 20 months, still more preferably about 24 months, when stored at 2-8° C. for instance. Methods for monitoring the stability of the antibody formulation of the present invention are available in the art, and include the methods described in the examples disclosed herein.

The term "stabilizing agent", or "stabilizer", as used herein, is a compound which improves the solubility of an active ingredient (such as tocilizumab) and stabilize said active ingredient against aggregate formation. It can also inhibit or reduce the reaction rate of the active ingredient with other compound(s) in a formulation. Examples of stabilizers for formulation are amino acids or proteins (e.g. glycine, arginine, albumin), organic acids (e.g. lactic acid or its salt lactate) or sugars (e.g. dextrose, mannitol, sucrose or lactose). According to the present invention, the preferred stabilizing agents are lactate, lactic acid and/or arginine.

The term "isotonicity agent" or "tonicifier", as used herein, is a compound that is physiologically tolerated and imparts a suitable tonicity to a formulation. It prevents notably the net flow of water across cell membranes that are in contact with the formulation. Compounds such as glycerin, are commonly used for such purposes. According to the present invention, the preferred isotonicity agent is a salt, even more preferably sodium chloride (NaCl).

The term "surfactant", as used herein, refers to a soluble compound that can be used notably to increase the water solubility of hydrophobic, oily substances or otherwise increase the miscibility of two substances with different hydrophobicities. For this reason, these polymers are commonly used in industrial applications, cosmetics, and pharmaceuticals. They are also used as model systems for drug delivery applications, notably in order to modify the absorption of the drug or its delivery to the target tissues. Well known surfactants include polysorbates (polyoxyethylene derivatives, also known as Tweens®) as well as poloxamers (i.e. copolymers based on ethylene oxide and propylene oxide, also known as Pluronics®). According to the invention, the preferred surfactant is a polysorbate surfactant and even more preferably the surfactant is polysorbate 80.

Herein, references to specific amounts of a given component of a composition, especially a buffering agent, suitably relate to the amounts of the pure anhydrous form of the relevant component (or compositions formed by using said amounts of the pure anhydrous form), even though such a component may be used in a non-anhydrous form when forming the composition. Amounts of any corresponding non-anhydrous forms (e.g. monohydrates, dihydrates, etc.) may be readily calculated by simply using the appropriate multiplier. For instance, unless stated otherwise (as per the Examples, where quantities relate to histidine), amounts stipulated in relation to histidine refer to the anhydrous form of histidine which has a molecular weight of about 155 g/mol. The skilled person would readily understand how to judiciously adjust the quantity of diluent/water depending on the form of the components used, in order to derive the target concentrations.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

Where a composition is said to comprise a plurality of ingredients (optionally in specific amounts of concentrations or in specific ranges of concentrations), said composition may optionally include additional ingredients other than those specifically mentioned.

DETAILED DESCRIPTION OF THE INVENTION

The main object of the present invention is a liquid pharmaceutical composition comprising the antibody tocilizumab, said antibody being able to neutralize (alternatively inhibit or antagonize) IL-6R activity. Said tocilizumab pharmaceutical composition preferably comprises histidine as a buffering agent keeping the pH in the range of 5.5 to 7.0 and a stabilizer selected from lactic acid or salts thereof. The composition is preferably (substantially or entirely) free of methionine. In addition, the composition may include any one or more additional components defined herein in relation to a liquid pharmaceutical composition (e.g. including tonicifier, surfactant, etc.), optionally in any amount, concentration, or form stipulated herein; and wherein the composition optionally exhibits any one or more parameters or properties given herein in relation to a liquid pharmaceutical composition (e.g. pH, osmolality). Preferably, the liquid pharmaceutical composition according to the invention comprises tocilizumab, histidine as a buffering agent keeping the pH in the range of 5.5 to 7.0, and a stabilizer selected from lactic acid or salts thereof, a polysorbate surfactant, a free amino acid and optionally a salt as an isotonicity agent. The free amino acid can also be used as a further stabilizer.

According to the present invention as a whole, the liquid pharmaceutical composition is (substantially or entirely) free of methionine (such as L-methionine).

The liquid pharmaceutical composition according to the present invention as a whole comprises tocilizumab at a concentration of or of about 10 to or to about 250 mg/ml, preferably of or of about 15 to or to about 200 mg/mL. For example, tocilizumab may be present in the formulation at a concentration of or of about 15, 20, 30, 40, 50, 60, 80, 100, 120, 140, 160, 180 or 200 mg/ml.

Preferably the formulations of the invention retain at least 80% of the anti-IL-6R biological activity at the time of formulation and/or packaging over a period of at least 12 months (before the first use). Anti-IL-6R activity may be measured by any known methods.

The liquid pharmaceutical composition according to the present invention as a whole has a pH in the range of or of about 5.5 to or to about 7.0. Preferably, the liquid pharmaceutical composition has a pH in the range of or of about 5.5 to or to about 6.5. Suitably, the liquid pharmaceutical composition has a pH of or of about 5.8 to 6.2 such as about 6.0.

The buffering agent according to the present invention is histidine and is at a concentration of or of about 10 to or to about 25 mM. In an embodiment, histidine is present at a concentration of or of about 15 to or to about 25 mM, preferably at a concentration of between 20 and 25 mM, even preferably at a concentration of or of about 21 mM.

Alternatively, the liquid pharmaceutical composition comprises the buffering agent (suitably histidine buffering species—e.g. histidine itself) at a concentration of or of about 0.1 to or to about 10 mg/mL. In an embodiment, the buffering agent is present at a concentration of or of about 0.5 to or to about 5 mg/mL, more preferably of between 2 and 4 mg/mL. For example, the buffering agent may be present in the formulation at a concentration of or of about 2.0, 2.25, 2.5, 2.75, 3.0, 3.25, 3.5, 3.75 or 4.0 mg/mL. In an embodiment, the buffering agent is histidine (such as L-histidine) and is present at a concentration of or of about 3.25 mg/mL.

Alternatively, the liquid pharmaceutical composition comprises the buffering agent (suitably histidine buffering species—e.g. histidine itself) in a molar ratio of buffering agent to tocilizumab of from about 5:1 to about 200:1, and will mainly depend on the concentration of tocilizumab in the formulation. For instance, when tocilizumab is at 20 mg/mL the molar ratio is most suitably about 145:1 and when tocilizumab is at 180 mg/mL the molar ratio is most suitably about 17:1.

The liquid pharmaceutical composition according to the invention as a whole comprises a stabilizing agent, most preferably either sodium lactate or lactic acid. Sodium lactate and lactic acid were indeed both identified by the inventors as particularly advantageous stabilizing agents for use together with histidine in liquid tocilizumab formulations.

The liquid pharmaceutical composition comprises the stabilizing agent (such as sodium lactate or lactic acid) at a concentration of or of about 1 to or to about 20 mM, preferably of or of about 5 to or to or to about 15 mM, more preferably from of from about 8 to or to about 12 mM. In a particular embodiment, the stabilizing agent is sodium lactate or lactic acid and is present in the liquid pharmaceutical composition at a concentration of or of about 10 mM.

Alternatively, the liquid pharmaceutical composition comprises the stabilizing agent (such as sodium lactate or lactic acid) at a concentration of or of about 0.5 mg/mL to or to about 5 mg/mL, more preferably of or of about 1 mg/mL to or to about 2 mg/mL, even more preferably of or of about 1.15 mg/mL. In a particular embodiment, the stabilizing agent is sodium lactate or lactic acid and is present in the liquid pharmaceutical composition at a concentration of or of about 1.12 mg/mL. Alternatively, the liquid pharmaceutical composition comprises the stabilizing agent (such as sodium lactate or lactic acid) in a molar ratio of stabilizing agent to tocilizumab of from about 5:1 to about 100:1, and will mainly depend on the concentration of tocilizumab in the formulation. For instance, in a composition comprising 20 mg/mL tocilizumab the molar ratio is most suitably about 72:1 and in a composition comprising 180 mg/mL tocilizumab the molar ratio is most suitably about 8:1.

The liquid pharmaceutical composition according to the present invention as a whole comprises at least one free amino acid other than histidine and methionine. Preferably, said free amino acid is arginine. Said component has also been shown to be a good stabilizer.

The liquid pharmaceutical composition comprises the at least one free amino acid (such as arginine) at a concentration of or of about 50 to or to about 150 mM, preferably of or of about 75 to or to about 125 mM, more preferably of or of about 90 to or to about 110 mM. For instance, the free amino acid is present at a concentration of or of about 90, 95, 100, 105 or 110 mM. In a particular embodiment, the at least one free amino acid is arginine (such as L-arginine) and is present in the liquid pharmaceutical composition at a concentration of or of about 100 mM.

Alternatively, the liquid pharmaceutical composition comprises the at least one free amino acid (such as arginine) at a concentration of or of about 10 mg/mL to or to about 25 mg/mL, preferably of or of about 15 mg/mL to or to about 20 mg/mL, more preferably of or of about 16 mg/mL to or to about 18 mg/mL. For instance, the at least one free amino acid(s) is/are present at a concentration of or of about 16.0, 16.5, 17.0, 17.5 or 18.0 mg/mL. In a particular embodiment, the at least one free amino acid is arginine (such as L-arginine) and is present in the liquid pharmaceutical composition at a concentration of or of about 17.4 mg/mL.

Alternatively, the liquid pharmaceutical composition comprises the at least one free amino acid (such as arginine) in a molar ratio of free amino acid to tocilizumab of from about of from about 50:1 to about 800:1, and will mainly depend on the concentration of antibody in the formulation. For instance, in a composition comprising 20 mg/mL tocilizumab the molar ratio is preferably about 725:1 and in a composition comprising 180 mg/mL tocilizumab the molar ratio is most suitably about 80:1.

The liquid pharmaceutical composition according to the present invention as a whole contains surfactants. Preferred surfactants are polysorbates, such as polysorbate 20 (alternative name: polyoxyethylene (20) sorbitan monolaurate), polysorbate 40 (alternative name: polyoxyethylene (20) sorbitan monopalmitate), polysorbate 60 (alternative name: polyoxyethylene (20) sorbitan monostearate) or polysorbate 80 (alternative name: polyoxyethylene (20) sorbitan monooleate, or Tween 80®). Preferably the surfactant is polysorbate 80.

The liquid pharmaceutical composition comprises the surfactant, such as polysorbate 80, at a concentration of or of about 0.05 to or to about 0.5 mM, preferably of or of about 0.075 to or to about 0.3 mM, more preferably of or of about 0.1 to or to about 0.2 mM. For instance, the surfactant is present at a concentration of or of about 0.10, 0.11, 0.12, 0.13, 0.14, 0.15, 0.16, 0.17, 0.18, 0.19 or 0.2 mM. In a particular embodiment, the surfactant is polysorbate 80 and is present in the liquid pharmaceutical composition at a concentration of or of about 0.152 mM.

Alternatively, the liquid pharmaceutical composition comprises the surfactant, such as polysorbate 80, at a concentration of or of about 0.05 to or to about 1 mg/mL, preferably of or of about 0.1 to or to about 1 mg/mL, more preferably of or of about 0.15 to or to about 0.3 mg/mL. For instance, the surfactant is present at a concentration of or of about 0.15, 0.16, 0.17, 0.18, 0.19, 0.20, 0.21, 0.22, 0.23, 0.24, 0.25 or 0.3 mg/mL. In a particular embodiment, the surfactant is polysorbate 80 and is present in the liquid pharmaceutical composition at a concentration of or of about 0.2 mg/mL.

Alternatively, the liquid pharmaceutical composition comprises the surfactant (such as polysorbate 80) in a molar ratio of surfactant to tocilizumab of from about 1:15 to about 15:10, and will mainly depend on the concentration of antibody in the formulation. For instance, in a composition comprising 20 mg/mL tocilizumab the molar ratio is preferably about 11:10 and in a composition comprising 180 mg/mL tocilizumab the molar ratio is most suitably about 1:8.

The liquid pharmaceutical compositions of the invention may include any one or more pharmaceutically acceptable diluents, or mixture thereof. However, most suitably the liquid pharmaceutical composition is an aqueous pharmaceutical composition. Most suitably the diluent is water, and suitably water alone. The water is suitably water for injection (WFI). The diluent may constitute the balance of ingredients in any liquid pharmaceutical composition, for instance so that the weight percentages total 100%. Any concentrations given herein in relation to any component of the liquid pharmaceutical composition represent concentrations of said component in (and suitably dissolved in) the diluent in admixture with any other components.

The liquid pharmaceutical composition of the invention is suitably a solution, and is preferably (substantially or entirely) free of particulates or precipitates.

The liquid pharmaceutical composition according to the present invention as a whole may further comprise one or more excipients such as a salt (acting as an isotonicity agent). In a particular embodiment, the isotonicity agent is or comprises sodium chloride (NaCl). In a particular embodiment, the isotonicity agent is sodium chloride. Sodium chloride is a particularly advantageous isotonicity agent for use together with the histidine buffer in liquid tocilizumab formulations.

Suitably, the liquid pharmaceutical composition comprises the salt (such as sodium chloride) at a concentration of or of about 5 to or to about 50 mM, preferably of or of about 10 to or to about 30 mM, such as about 10, 12.5, 15, 17.5, 20, 22.5, 25, 27.5, or 30 25 mM. In an embodiment, the salt is present at a concentration of or of about 10 mM. In a particular embodiment, the salt is sodium chloride and is present at a concentration of or of about 10 mM.

Alternatively, the liquid pharmaceutical composition comprises the salt (such as NaCl) at a concentration of or of about 0.1 mg/mL to or to about 5 mg/mL, preferably of or of about 0.25 mg/mL to or to about 2.5 mg/mL, more suitably of or of about 0.4 mg/mL to or to about 2 mg/mL. In an embodiment, the salt is present at a concentration of or of about 0.5 mg/mL to or to about 1.2 mg/mL, most suitably about 0.58 mg/mL. In a particular embodiment, the salt is sodium chloride and is present at a concentration of about 0.58 mg/mL.

Alternatively, the liquid pharmaceutical composition comprises the salt (such as NaCl) in a molar ratio of salt to tocilizumab of from about 2:1 to about 100:1, and will mainly depend on the concentration of tocilizumab in the formulation. For instance, in a composition comprising 20 mg/mL tocilizumab the molar ratio is preferably about 72:1 and in a composition comprising 180 mg/mL tocilizumab the molar ratio is most suitably about 8:1.

In a further aspect, the present invention also provides a method of stabilizing liquid tocilizumab compositions, comprising mixing tocilizumab with any relevant components required to form a liquid pharmaceutical composition as defined herein. Therefore, herein provided is a method of manufacturing a liquid pharmaceutical composition, the method comprising mixing together tocilizumab, a histidine buffer and lactic acid or salts thereof, a polysorbate surfactant, a free amino acid and optionally a salt (such as NaCl, as an isotonicity agent). Each of these compounds (i.e. tocilizumab, histidine buffer, lactic acid or salts thereof, the surfactant, the at least one free amino acid, and/or the salt) can be used according to the concentrations, pH, and/or ratios described herein. If needed, the skilled person may refer to the example section which follow or techniques well known in the art for forming liquid pharmaceutical compositions (especially those for injection via syringe).

In an embodiment, the method involves mixing together the relevant components in a diluent (e.g. water), so that all of the components are (substantially or entirely) dissolved in the diluent.

Also provided is a liquid pharmaceutical composition obtainable by, obtained by, or directly obtained by a method of manufacturing a liquid pharmaceutical composition as defined herein.

Suitably, the liquid pharmaceutical compositions of the invention have a shelf life of at least 6 months, suitably at least 12 months, suitably at least 18 months, more suitably at least 24 months. Suitably, the liquid pharmaceutical compositions of the invention have a shelf life of at least 6 months, suitably at least 12 months, suitably at least 18 months, more suitably at least 24 months, at a temperature of 2-8° C.

The final liquid pharmaceutical composition may be filtered, suitably to remove particulate matter. Suitably filtration is through filters sized at or below 1 μm, suitably at 0.22 μm. For instance, filtration is made through PES filters or PVDF filters at 0.22 μm.

In a further aspect, the present invention provides a drug delivery device comprising a liquid pharmaceutical composition as defined herein. Preferably the drug delivery device comprises a chamber within which the pharmaceutical composition resides. More preferably, the drug delivery device is sterile.

The drug delivery device may be a vial, ampoule, syringe, injection pen (e.g. essentially incorporating a syringe), or intravenous bag. When the drug delivery device is a syringe, it is preferably an injection pen. Suitably the syringe is a glass syringe.

In yet a further aspect, the present invention provides a kit of parts comprising a drug delivery device (without the liquid pharmaceutical composition incorporated therein), a liquid pharmaceutical composition as defined herein (optionally contained in a separate package or container), and optionally a set of instructions with directions regarding the administration (e.g. sub-cutaneous or intravenous) of the liquid pharmaceutical composition. The user may then fill the drug delivery device with the liquid pharmaceutical composition (which may be provided in a vial or ampoule or such like) prior to administration.

Also described is a package comprising a liquid pharmaceutical composition as defined herein. Suitably the package comprises a drug delivery device as defined herein, suitably a plurality of drug delivery devices. The package may comprise any suitable container for containing one or more drug delivery devices.

The present invention further provides a method of manufacturing a drug delivery device, suitably as defined herein, the method comprising incorporating a liquid pharmaceutical composition as defined herein within a drug delivery device. Such manufacture typically involves charging the liquid pharmaceutical composition as defined herein to a syringe, suitably via a needle affixed thereto. The needle may thereafter be removed, replaced, or remain. Also disclosed is a drug delivery device obtainable by, obtained by, or directly obtained by a method of manufacture defined herein. Also described is a method of manufacturing a package, the method comprising incorporating a liquid pharmaceutical composition as defined herein within a package. Suitably this is achieved by incorporating said liquid pharmaceutical composition within one or more drug delivery devices, and thereafter incorporating the one or more pre-filled drug delivery devices into a container present within the package. The present invention provides, in addition, a package obtainable by, obtained by, or directly obtained by a method of manufacture defined herein.

The liquid pharmaceutical compositions defined herein may be used to treat any one or more of the aforementioned diseases or medical disorders. In a particular embodiment, the liquid pharmaceutical compositions are used to treat rheumatoid arthritis and/or juvenile idiopathic arthritis. Alternatively, the liquid pharmaceutical compositions are used to treat other diseases such as giant cell arteritis or systemic sclerosis.

The liquid pharmaceutical compositions are suitably parenterally administered, either via intravenous injection or via sub-cutaneous injection.

Particular Embodiments

In an embodiment, the liquid pharmaceutical composition comprises:
tocilizumab;
a histidine buffer, keeping the pH between about 5.5 to 7.0;
stabilizer selected from lactic acid or salts thereof;
a free amino acid (e.g. arginine);
a surfactant (e.g. polysorbate 80);
water for injection; and
optionally a salt (e.g. NaCl).

In an embodiment, the liquid pharmaceutical composition comprises:
tocilizumab at a concentration of 10 to 250 mg/mL;
a histidine buffer, keeping the pH between about 5.5 to 7.0;
stabilizer selected from lactic acid or salts thereof;
a free amino acid (e.g. arginine);
a surfactant (e.g. polysorbate 80);
water for injection; and
optionally a salt (e.g. NaCl).

In an embodiment, the liquid pharmaceutical composition comprises:
tocilizumab;
a histidine buffer, keeping the pH between about 5.5 to 7.0, wherein the buffer is at a concentration of 10 to 25 mM, or alternatively at a concentration of 0.5 to 5 mg/mL or alternatively at a molar ratio buffer to antibody of 5:1 to 200:1;
stabilizer selected from lactic acid or salts thereof;
a free amino acid (e.g. arginine);
a surfactant (e.g. polysorbate 80);
water for injection; and
optionally a salt (e.g. NaCl).

In an embodiment, the liquid pharmaceutical composition comprises:
tocilizumab;
a histidine buffer, keeping the pH between about 5.5 to 7.0;
a stabilizer selected from lactic acid or salts thereof, wherein the stabilizer is at a concentration of 5 to 15 mM, or alternatively at a concentration of 0.5 to 5 mg/mL or alternatively at a molar ratio stabilizer to antibody of 5:1 to 100:1;
a free amino acid (e.g. arginine);
a surfactant (e.g. polysorbate 80);
water for injection; and
optionally a salt (e.g. NaCl).

In an embodiment, the liquid pharmaceutical composition comprises:
tocilizumab;
a histidine buffer, keeping the pH between about 5.5 to 7.0;
stabilizer selected from lactic acid or salts thereof;
a free amino acid (e.g. arginine), wherein the free amino acid is at a concentration of 50 to 150 mM, or alternatively at a concentration of 10 to 25 mg/mL or alternatively at a molar ratio free amino acid to antibody of 50:1 to 800:1;
a surfactant (e.g. polysorbate 80);
water for injection; and
optionally a salt (e.g. NaCl).

In an embodiment, the liquid pharmaceutical composition comprises:
tocilizumab;
a histidine buffer, keeping the pH between about 5.5 to 7.0;
stabilizer selected from lactic acid or salts thereof;
a free amino acid (e.g. arginine);
a surfactant (e.g. polysorbate 80), wherein the surfactant is at a concentration of 0.05 to 0.55 mM, or alternatively at a concentration of 0.05 to 1 mg/mL or alternatively at a molar ratio surfactant to antibody of 1:15 to 15:10;
water for injection; and
optionally a salt (e.g. NaCl).

In an embodiment, the liquid pharmaceutical composition comprises:
tocilizumab;
a histidine buffer, keeping the pH between about 5.5 to 7.0;
stabilizer selected from lactic acid or salts thereof;
a free amino acid (e.g. arginine);
a surfactant (e.g. polysorbate 80);
water for injection; and
optionally a salt (e.g. NaCl), wherein the salt is at a concentration of 5 to 50 mM, or alternatively at a concentration of 0.1 to 5 mg/mL or alternatively at a molar ratio salt to antibody of 2:1 to 100:1.

In an embodiment, the liquid pharmaceutical composition comprises:
tocilizumab at a concentration of 10 to 250 mg/mL;
a histidine buffer, keeping the pH between about 5.5 to 7.0, wherein the buffer is at a concentration of 10 to 25 mM, or alternatively at a concentration of 0.5 to 5 mg/mL or alternatively at a molar ratio buffer to antibody of 5:1 to 200:1
a stabilizer selected from lactic acid or salts thereof, wherein the stabilizer is at a concentration of 5 to 15 mM, or alternatively at a concentration of 0.5 to 5 mg/mL or alternatively at a molar ratio stabilizer to antibody of 5:1 to 100:1;
a free amino acid (e.g. arginine), wherein the free amino acid is at a concentration of 50 to 150 mM, or alternatively at a concentration of 10 to 25 mg/mL or alternatively at a molar ratio free amino acid to antibody of 50:1 to 800:1;
a surfactant (e.g. polysorbate 80), wherein the surfactant is at a concentration of 0.05 to 0.55 mM, or alternatively at a concentration of 0.05 to 1 mg/mL or alternatively at a molar ratio surfactant to antibody of 1:15 to 15:10;

water for injection; and optionally a salt (e.g. NaCl), wherein the salt is at a concentration of 5 to 50 mM, or alternatively at a concentration of 0.1 to 5 mg/mL or alternatively at a molar ratio salt to antibody of 2:1 to 100:1.

EXAMPLES

Materials and Equipment

The following materials were used in the preparation of formulations described in the examples:

| Chemical | Supplier |
|---|---|
| L-histidine | Fisher |
| L-Arginine | Sigma |
| L-methionine | Sigma |
| Sodium-L-lactate | Sigma |
| L-lactic acid | Sigma |
| Sodium chloride | Sigma |
| Sodium bisulphite | Sigma |
| Sodium-L-ascorbate | Sigma |
| L-Tryptophan | Sigma |
| Polysorbate 80 | Sigma |
| Water for injection | HyClone |

Analytical Techniques and Protocols

The following analytical methods of protocols were employed, in the examples and screening experiments which follow, for the reasons stated in the table below:

| Analytical Method | Scope of the test |
|---|---|
| SEC | Quantification of soluble aggregates |
| IEX-HPLC | Quantification of acidic and basic species |
| Visual inspection | Appearance, assessment of particle formation |

The individual protocols for each of the above analytical methods are described in turn below, and references in the examples and screening experiments to any such analytical methods used these protocols.

Size Exclusion Chromatography (SEC)

High performance size exclusion chromatography of tocilizumab preparations was performed using the Dionex Ultimate 3000 UHPLC® focused system with a 5 μm phase diol Silica 250 Å pore packing material in a 300 mm by 7.8 mm column. The column was equilibrated in 200 mM sodium phosphate buffer, 250 mM NaCl, pH 7.0 mobile phase. Flow rate was 0.5 mL/min and UV detection (280 nm) was used. Injection volume was 20 μL. All analyses were performed at ambient temperature.

Ion-Exchange Chromatography (IEX-HPLC)

High performance ion exchange chromatography of tocilizumab preparations was performed using the Agilent technologies 1200 series HPLC® system with a 7 μm particle in a 100 mm by 4.6 mm column. The column was equilibrated in 20 mM sodium phosphate buffer pH7, 250 mM NaCl, pH 7.0 mobile phase and elution was performed with a gradient method by 20 mM sodium phosphate buffer, 1M NaCl pH 7.0. Flow rate was 0.3 mL/min and UV detection (214 nm and 280 nm) was used. Injection volume was 10 μL. All analyses were performed at 40° C.

Visual Inspection

Visible particles were suitably detected using the 2.9.20. European Pharmacepoeia Monograph (Particulate Contamination: Visible Particles). The apparatus consists of a viewing station comprising:

a matt black panel of appropriate size held in a vertical position a non-glare white panel of appropriate size held in a vertical position next to the black panel an adjustable lampholder fitted with a suitable, shaded, white-light source and with a suitable light diffuser (a viewing illuminator containing two 13 W fluorescent tubes, each 525 mm in length, is suitable). The intensity of illumination at the viewing point is maintained between 2000 lux and 3750 lux.

Any adherent labels were removed from the container and the outside washed and dried. The container was gently swirled or inverted, ensuring that air bubbles were not introduced, and observed for about 5 s in front of the white panel. The procedure was repeated in front of the black panel. The presence of any particles was recorded.

Example 1—Testing of the Effect of Alternative Antioxidants on Aggregation of Tocilizumab Commercial subcutaneous (sc) formulation (ACTEMRA®) of tocilizumab comprise the following ingredients:

| Ingredients of the sc formulation |
|---|
| Tocilizumab (180 mg/mL) |
| polysorbate 80, |
| L-histidine and L-histidine monohydrochloride |
| L-arginine and L-arginine hydrochloride |
| L-methionine |
| water for injection (WFI) |
| pH of about 6.0 |

Methionine was shown to inhibit considerably the formation of high molecular species (HMWS) of tocilizumab during storage, as measured by gel permeation chromatography (also known as size exclusion chromatography, SEC). The rate of formation of HMWS (in the form of a dimer) was shown to be considerably lower in compositions containing arginine and methionine compared with the composition containing arginine only; see, e.g., example 1 of EP2238985. However, whilst methionine is an approved inactive ingredient in approved pharmaceutical products, there are certain downsides to using it due to its propensity to oxidise rapidly, particularly above the refrigeration temperatures, leading to concerns about its stability during processing and storage as well as development of a malodour due to the oxidised methionine species. Therefore, it is better to avoid this compound whenever possible. Methionine having a known antioxidant activity, the effect of alternative antioxidants was tested on the formation of High Molecular Weight Species (HMWS) of tocilizumab (180 mg/ml) during storage at 45° C. The effect was tested in a background formulation comprising:

L-histidine (21 mM)
L-arginine (100 mM)
polysorbate 80 (0.2 mg/ml)
water for injection
pH 6.0

Aggregation of tocilizumab was assessed by SEC and visual assessment prior to and following storage at 45° C. for 2 weeks.

Results are shown in Table 1. Two of the antioxidants tested, sodium bisulphite and sodium ascorbate, resulted in a very rapid formation of HMWS. In addition, the use of sodium ascorbate resulted to visual precipitation after 2 weeks at 45° C. Whilst the use of both sodium lactate and tryptophan resulted in a significantly lower rate of HMWS formation, it was only sodium lactate that led to HMWS formation that was comparable (albeit still slightly higher) to that achieved in the presence of methionine. Importantly, unlike other antioxidants such as methionine, sodium lactate is also known to be very stable during storage. Consequently, sodium lactate was selected as the key stabilizing species to be taken into further optimization described in subsequent examples.

Aggregation of tocilizumab was assessed by SEC and visual assessment prior to and following storage at 40° C. for 4 weeks and 25° C. for 8 weeks.

Results are shown in Table 2. It was shown that the rate of increase in HMWS was greater in the absence of methionine compared with an identical composition that contained methionine (30 mM), confirming the stabilizing effect of methionine reported previously by others (EP2238985). It was also shown that sodium lactate inhibited the formation of HMWS. The stabilizing effect of sodium lactate appeared to be somewhat more pronounced at 10 mM concentration compared with higher concentrations (25 mM and 50 mM). Using 10 mM sodium lactate, the inhibition of HMWS formation was comparable with that observed using methionine (30 mM).

TABLE 2

Effect of methionine and sodium lactate on the increase in % HMWS and visual assessment of tocilizumab compositions after storage at 40° C. for 4 weeks and 25° C. for 8 weeks. All formulations contained L-histidine (21 mM), L-arginine (100 mM), polysorbate 80 (0.2 mg/ml) and WFI and adjusted to pH 6.0.

| Additive | % increase in HMWS (4 weeks at 40° C.) | Visual assessment (4 weeks at 40° C.) | % increase in HMWS (8 weeks at 25° C.) | Visual assessment (8 weeks at 25° C.) |
|---|---|---|---|---|
| Methionine (30 mM) | 0.23 | Pass | 0.07 | Pass |
| No additive | 0.42 | Pass | 0.19 | Pass |
| Sodium lactate (50 mM) | 0.32 | Pass | 0.10 | Pass |
| Sodium lactate (25 mM) | 0.33 | Pass | 0.10 | Pass |
| Sodium lactate (10 mM) | 0.28 | Pass | 0.08 | Pass |

Pass = clear solution free of visible particles;
Fail = formation of particles and/or opalescence.

TABLE 1

Effect of selected antioxidants on the increase in % HMWS and visual assessment of tocilizumab compositions after storage at 45° C. for 2 weeks. All formulations contained L-histidine (21 mM), L-arginine (100 mM), polysorbate 80 (0.2 mg/ml) and WFI and were adjusted to pH 6.0.

| Additive | % increase in HMWS (2 weeks at 45° C.) | Visual assessment (2 weeks at 45° C.) |
|---|---|---|
| Methionine (30 mM) | 0.35 | Pass |
| Lactate (50 mM) | 0.42 | Pass |
| Sodium bisulphite (30 mM) | 20.56 | Pass |
| Sodium ascorbate (10 mM) | 9.06 | Fail |
| Tryptophane (7 mM) | 0.56 | Pass |

Pass = clear solution free of visible particles;
Fail = formation of particles and/or opalescence.

Example 2—Investigation of the Effect of Lactate Concentration on Aggregation of Tocilizumab The effect of sodium lactate concentration on the formation of HMWS of tocilizumab (180 mg/ml) during storage at 40° C. and 25° C. was assessed. The effect was compared to that of methionine (30 mM) and also to a composition that did not contain any antioxidant. The effect was tested in a background formulation comprising:
  L-histidine (21 mM)
  L-arginine (100 mM)
  polysorbate 80 (0.2 mg/ml)
  water for injection (WFI)
  pH 6.0

Example 3—Further Stability Testing of Lactate-Based Formulation

Stability of tocilizumab was tested in both the subcutaneous-like (180 mg/ml) and the intravenous-like formulation of ACTEMRA® (20 mg/ml) alongside a selected lactate-based formulation.

The subcutaneous (sc)-like formulation of ACTEMRA® contained tocilizumab (180 mg/ml), L-histidine (20 mM), L-arginine (100 mM), L-methionine (30 mM), polysorbate 80 (0.2 mg/ml) and water for injection (WFI) and was adjusted to pH 6.0.

The intravenous (iv)-like formulation of ACTEMRA® contained tocilizumab (20 mg/ml), disodium phosphate dodecahydrate and sodium dihydrogen phosphate dehydrate (as a 15 mM phosphate buffer), polysorbate 80 (0.5 mg/ml), sucrose (50 mg/ml) and WFI and was adjusted to pH 6.5.

The same lactate-based composition was used both for the 180 mg/ml and for the 20 mg/ml tocilizumab samples. The composition contained L-histidine (21 mM), L-arginine (100 mM), sodium L-lactate (10 mM) polysorbate 80 (0.2 mg/ml) and WFI and was adjusted to pH 6.0.

The rate of HMWS formation was assessed by size exclusion chromatography. Ion-exchange chromatography was used to assess the rate of formation of acidic and basic species.

The results relating to the 180 mg/ml tocilizumab compositions are shown in Tables 3 and 4. Both samples passed the visual assessment test after 4 weeks incubation at 40° C. (Table 3). The rate of HMWS formation was comparable between the formulation of ACTEMRA® and the lactate-based formulation (Table 3). Similarly, the rate of formation of acidic species and basic species was comparable between the formulation of ACTEMRA® and the lactate-based formulation (Table 4).

TABLE 3

Visual assessment and % HMWS in sc-like and lactate-based formulations at T = 0 and after storage at 40° C. for 4 weeks. Concentration of tocilizumab = 180 mg/ml.

| Formulation | Visual assessment (T = 0) | Visual assessment (4 weeks) | % HMWS (T = 0) | % HMWS (4 weeks) |
|---|---|---|---|---|
| Formulation of ACTEMRA ®) | Pass | Pass | 0.70 | 0.84 |
| Lactate-based formulation | Pass | Pass | 0.72 | 0.89 |

Pass = clear solution free of visible particles;
Fail = formation of particles and/or opalescence.

TABLE 4

Assessment of acidic and basic species in sc-like and lactate-based formulations at T = 0 and after storage at 40° C. for 4 weeks. Concentration of tocilizumab = 180 mg/ml.

| Formulation | Acidic species (T = 0) | Acidic species (4 weeks) | Basic species (T = 0) | Basic species (4 weeks) |
|---|---|---|---|---|
| Formulation of ACTEMRA ®) | 11.14 | 20.51 | 9.54 | 11.14 |
| Lactate-based formulation | 11.18 | 20.68 | 9.04 | 11.91 |

The results relating to the 20 mg/ml tocilizumab compositions are shown in Tables 5 and 6. Both samples passed the visual assessment test after 4 weeks incubation at 40° C. (Table 5). There appeared to be a slight decrease in HMWS following the 4 weeks incubation at 40° C., the decrease being more pronounced in the lactate-based formulation (Table 5). The cause for the decrease is not entirely clear, and it is not certain whether a degree of HMWS dissociation occurred or whether the change is within the analytical error. In any case, incubation at 40° C. did not lead to an increase in HMWS in either of the two formulations tested. The lactate-based formulation appeared to show a significantly lower rate of acidic species formation compared with the intravenous-like formulation (Table 6). This is most likely due to the different in pH of the lactate-based formulation (pH 6.0) and of the intravenous-like formulation (pH 6.5). The difference in pH can also explain a slightly higher rate of basic species formation in the lactate-based formulation compared with the intravenous-like formulation. Overall, the increase in total charge impurities (i.e. sum of acidic species and basic species) was considerably lower in in the lactate-based formulation compared with the intravenous-like formulation following incubation at 40° C. (Table 6).

TABLE 5

Visual assessment and % HMWS in iv-like and lactate-based formulations at T = 0 and after storage at 40° C. for 4 weeks. Concentration of tocilizumab = 20 mg/ml.

| Formulation | Visual assessment (T = 0) | Visual assessment (4 weeks) | % HMWS (T = 0) | % HMWS (4 weeks) |
|---|---|---|---|---|
| Formulation of ACTEMRA ®) | Pass | Pass | 0.68 | 0.60 |
| Lactate-based formulation | Pass | Pass | 0.65 | 0.41 |

Pass = clear solution free of visible particles;
Fail = formation of particles and/or opalescence.

TABLE 6

Assessment of acidic and basic species in iv-like and lactate-based formulations at T = 0 and after storage at 40° C. for 4 weeks. Concentration of tocilizumab = 20 mg/ml.

| Formulation | Acidic species (T = 0) | Acidic species (4 weeks) | Basic species (T = 0) | Basic species (4 weeks) |
|---|---|---|---|---|
| Formulation of ACTEMRA ®) | 9.80 | 31.70 | 7.75 | 9.30 |
| Lactate-based formulation | 10.11 | 24.47 | 8.39 | 12.25 |

Example 4—Further Stability Testing of Lactic Acid-Based Formulation

Stability of tocilizumab was tested in the subcutaneous-like (180 mg/ml) formulation of ACTEMRA® alongside a selected lactic acid-based formulation.

The sc-like and iv-like formulations of ACTEMRA® were identical to the ones of example 3. Assessments of HMWS, acidic and basic species were performed as in Example 3.

The same lactic acid-based composition was used both for the 180 mg/ml and for the 20 mg/ml tocilizumab samples. The composition contained L-histidine (21 mM), L-arginine (100 mM), L-lactic acid (10 mM), sodium chloride (10 mM), polysorbate 80 (0.2 mg/ml), WFI and adjusted to pH 6.0. The results for the formulations comprising 180 mg/mL of tocilizumab are shown in Tables 7 to 12. The samples were evaluated after up to 8 weeks incubation at 40° C. (Tables 7 and 10), up to 26 weeks incubation at 25° C. (Tables 8 and 11) and up to 26 weeks incubation at 5° C. (Tables 9 and 12). All formulations passed the visual assessment test whatever the incubation length/temperature. The rate of HMWS formation was comparable between the formulation of ACTEMRA® and the lactic acid-based formulation at 25° C. (Table 8) and at 5° C. (Table 9) and was slightly higher after 8 weeks at 40° C. for the lactic acid-based formulation (Table 7). The rates of formation of acidic species were comparable between the formulation of ACTEMRA® and the lactic acid-based formulation at all temperatures (Tables 10 to 12) as well as the overall level of basic species.

TABLE 7

Visual assessment and % HMWS in sc-like and lactic acid-based formulations at T = 0 and after storage at 40° C. for 4 and 8 weeks. Concentration of tocilizumab = 180 mg/ml.

| Formulation | Visual assessment (T = 0) | Visual assessment (8 weeks) | % HMWS (T = 0) | % HMWS (4 weeks) | % HMWS (8 weeks) |
|---|---|---|---|---|---|
| Formulation of ACTEMRA ®) | Pass | Pass | 0.52 | 0.71 | 0.90 |
| Lactic acid-based formulation | Pass | Pass | 0.54 | 0.83 | 1.15 |

Pass = clear solution free of visible particles;
Fail = formation of particles and/or opalescence.

TABLE 8

Visual assessment and % HMWS in sc-like and lactic acid-based formulations at T = 0 and after storage at 25° C. for up to 26 weeks. Concentration of tocilizumab = 180 mg/ml. Pass = clear solution free of visible particles; Fail = formation of particles and/or opalescence.

| Formulation | Visual assessment (T = 0) | Visual assessment (26 weeks) | % HMWS (T = 0) | % HMWS (4 weeks) | % HMWS (8 weeks) | % HMWS (26 weeks) |
|---|---|---|---|---|---|---|
| Formulation of ACTEMRA ®) | Pass | Pass | 0.52 | 0.54 | 0.63 | 0.70 |
| Lactic acid-based formulation | Pass | Pass | 0.54 | 0.58 | 0.67 | 0.79 |

TABLE 9

Visual assessment and % HMWS in sc-like and lactic acid-based formulations at T = 0 and following storage at 5° C. up to 26 weeks. Concentration of tocilizumab = 180 mg/ml. Pass = clear solution free of visible particles; Fail = formation of particles and/or opalescence.

| Formulation | Visual assessment (T = 0) | Visual assessment (26 weeks) | % HMWS (T = 0) | % HMWS (4 weeks) | % HMWS (8 weeks) | % HMWS (26 weeks) |
|---|---|---|---|---|---|---|
| Formulation of ACTEMRA ®) | Pass | Pass | 0.52 | 0.54 | 0.57 | 0.59 |
| Lactic acid-based formulation | Pass | Pass | 0.54 | 0.56 | 0.60 | 0.63 |

TABLE 10

Assessment of acidic and basic species in sc-like and lactic acid-based formulations at T = 0 and after storage at 40° C. for 4 and 8 weeks. Concentration of tocilizumab = 180 mg/ml.

| Formulation | Acidic species (T = 0) | Acidic species (4 weeks) | Acidic species (8 weeks) | Basic species (T = 0) | Basic species (4 weeks) | Basic species (8 weeks) |
|---|---|---|---|---|---|---|
| Formulation of ACTEMRA ®) | 13.43 | 30.39 | 40.57 | 9.98 | 9.71 | 12.35 |
| Lactic acid-based formulation | 13.13 | 30.22 | 41.09 | 9.04 | 12.51 | 12.26 |

TABLE 11

Assessment of acidic and basic species in sc-like and lactic acid-based formulations at T = 0 and following storage at 25° C. for up to 26 weeks. Concentration of tocilizumab = 180 mg/ml.

| Formulation | Acidic species (T = 0) | Acidic species (4weeks) | Acidic species (8 weeks) | Acidic species (26 weeks) |
|---|---|---|---|---|
| Formulation of ACTEMRA ® | 13.43 | 20.22 | 20.79 | 25.59 |
| Lactic acid-based formulation | 13.13 | 14.10 | 21.30 | 25.34 |

| Formulation | Basic species (T = 0) | Basic species (4 weeks) | Basic species (8 weeks) | Basic species (26 weeks) |
|---|---|---|---|---|
| Formulation of ACTEMRA ® | 9.98 | 8.81 | 10.15 | 10.45 |
| Lactic acid-based formulation | 9.04 | 9.85 | 10.23 | 11.07 |

TABLE 12

Assessment of acidic and basic species in sc-like and lactic acid-based formulations at T = 0 and following storage at 5° C. for up to 26 weeks. Concentration of tocilizumab = 180 mg/ml.

| | Acidic species | Acidic species | Acidic species | Acidic species |
|---|---|---|---|---|
| Formulation of ACTEMRA ® | 13.43 | 14.14 | 14.02 | 13.65 |
| Lactic acid-based formulation | 13.13 | 14.69 | 14.00 | 14.45 |

| Formulation | Basic species (T = 0) | Basic species (4 weeks) | Basic species (8 weeks) | Basic species (26 weeks) |
|---|---|---|---|---|
| Formulation of ACTEMRA ® | 9.98 | 9.28 | 8.86 | 9.52 |
| Lactic acid-based formulation | 9.04 | 8.27 | 8.48 | 8.48 |

The results for the formulations comprising 20 mg/mL of tocilizumab are shown in Tables 13 to 18. The samples were evaluated in the same conditions than the formulations comprising 180 mg/mL of tocilizumab.

All formulations passed the visual assessment test whatever the incubation length/temperature. The rate of HMWS formation was comparable between the formulation of ACTEMRA® and the lactic acid-based formulation at 5° C. (Table 15) and was slightly higher after 8 weeks at 40° C. for the lactic acid-based formulation (Table 13). To the contrary, at 25° C. (Table 14) the level of HMWs decreased more significantly in the lactic acid based formulation after 4 weeks when compared to the formulation of ACTEMRA®, before reached a stable level from week 4 up to week 26. The cause for the decrease is not entirely clear, and it is not certain whether a degree of HMWS dissociation occurred or whether the difference is within the analytical error. The lactic acid-based formulation appeared to show a significantly lower rate of acidic species formation compared with the formulation of ACTEMRA® at 40° C. and 25° C. (Tables 16 to 17). This is most likely due to the different in pH of the lactic acid-based formulation (pH 6.0) and of the formulation of ACTEMRA® (pH 6.5). The difference in pH can also explain a slightly higher rate of basic species formation in the lactate-based formulation compared with the intravenous-like formulation. To the contrary, at 5° C. the level of acidic and basic species is globally stable over time for both formulations.

TABLE 13

Visual assessment and % HMWS in iv-like and lactate-based formulations at T = 0 and following storage at 40° C. for 8 weeks. Concentration of tocilizumab was 20 mg/ml.

| Formulation | Visual assessment (T = 0) | Visual assessment (8 weeks at 40° C.) | % HMWS (T = 0) | % HMWS (8 weeks at 40° C.) |
|---|---|---|---|---|
| Formulation of ACTEMRA ® | Pass | Pass | 0.50 | 1.03 |
| Lactic acid-based formulation | Pass | Pass | 0.49 | 1.11 |

Pass = clear solution free of visible particles;
Fail = formation of particles and/or opalescence.

TABLE 14

Visual assessment and % HMWS in iv-like and lactic acid-based formulations at T = 0 and following storage at 25° C. up to 26 weeks. Concentration of tocilizumab = 20 mg/ml. Pass = clear solution free of visible particles; Fail = formation of particles and/or opalescence.

| Formulation | Visual assessment (T = 0) | Visual assessment (26 weeks) | % HMWS (T = 0) | % HMWS (4 weeks) | % HMWS (8 weeks) | % HMWS (26 weeks) |
|---|---|---|---|---|---|---|
| Formulation of ACTEMRA ® | Pass | Pass | 0.50 | 0.44 | 0.48 | 0.56 |
| Lactic acid-based formulation | Pass | Pass | 0.49 | 0.37 | 0.38 | 0.37 |

TABLE 15

Visual assessment and % HMWS in iv-like and lactic acid-based formulations at T = 0 and after storage at 5° C. for up to 26 weeks. Concentration of tocilizumab = 20 mg/ml. Pass = clear solution free of visible particles; Fail = formation of particles and/or opalescence.

| Formulation | Visual assessment (T = 0) | Visual assessment (26 weeks) | % HMWS (T = 0) | % HMWS (4 weeks) | % HMWS (8 weeks) | % HMWS (26 weeks) |
|---|---|---|---|---|---|---|
| Formulation of ACTEMRA ® | Pass | Pass | 0.50 | 0.47 | 0.47 | 0.45 |

TABLE 15-continued

Visual assessment and % HMWS in iv-like and lactic acid-based formulations at T = 0 and after storage at 5° C. for up to 26 weeks. Concentration of tocilizumab = 20 mg/ml. Pass = clear solution free of visible particles; Fail = formation of particles and/or opalescence.

| Formulation | Visual assessment (T = 0) | Visual assessment (26 weeks) | % HMWS (T = 0) | % HMWS (4 weeks) | % HMWS (8 weeks) | % HMWS (26 weeks) |
|---|---|---|---|---|---|---|
| Lactic acid-based formulation | Pass | Pass | 0.49 | 0.44 | 0.44 | 0.41 |

TABLE 16

Assessment of acidic and basic species in iv-like and lactic acid-based formulations at T = 0 and after storage at 40° C. for 4 and 8 weeks. Concentration of tocilizumab = 20 mg/ml.

| Formulation | Acidic species (T = 0) | Acidic species (4 weeks) | Acidic species (8 weeks) | Basic species (T = 0) | Basic species (4 weeks) | Basic species (8 weeks) |
|---|---|---|---|---|---|---|
| Formulation of ACTEMRA ®) | 13.36 | 40.12 | 55.66 | 9.09 | 7.64 | 8.93 |
| Lactic acid-based formulation | 13.10 | 29.34 | 41.59 | 9.21 | 9.90 | 13.47 |

TABLE 17

Assessment of acidic and basic species in iv-like and lactic acid-based formulations at T = 0 and following storage at 25° C. for up to 26 weeks. Concentration of tocilizumab = 20 mg/ml.

| Formulation | Acidic species (T = 0) | Acidic species (4 weeks) | Acidic species (8 weeks) | Acidic species (26 weeks) |
|---|---|---|---|---|
| Formulation of ACTEMRA ®) | 13.36 | 22.19 | 23.60 | 32.96 |
| Lactic acid-based formulation | 13.10 | 19.33 | 20.32 | 24.23 |

| Formulation | Basic species (T = 0) | Basic species (4 weeks) | Basic species (8 weeks) | Basic species (26 weeks) |
|---|---|---|---|---|
| Formulation of ACTEMRA ®) | 9.09 | 9.19 | 9.37 | 7.77 |
| Lactic acid-based formulation | 9.21 | 8.89 | 10.41 | 9.79 |

TABLE 18

Assessment of acidic and basic species in iv-like and lactic acid-based formulations at T = 0 and following storage at 5° C. for up to 26 weeks. Concentration of tocilizumab = 20 mg/ml.

| Formulation | Acidic species (T = 0) | Acidic species (4 weeks) | Acidic species (8 weeks) | Acidic species (26 weeks) |
|---|---|---|---|---|
| Formulation of ACTEMRA ®) | 13.36 | 14.54 | 14.71 | 14.65 |
| Lactic acid-based formulation | 13.10 | 14.44 | 13.86 | 13.25 |

| Formulation | Basic species (T = 0) | Basic species (4 weeks) | Basic species (8 weeks) | Basic species (26 weeks) |
|---|---|---|---|---|
| Formulation of ACTEMRA ®) | 9.09 | 8.03 | 8.27 | 8.04 |
| Lactic acid-based formulation | 9.21 | 8.29 | 8.79 | 9.58 |

REFERENCES

1) WO03/068260
2) WO2009/084659
3) WO02/13860
4) WO2011/085158
5) WO2013/063510
6) EP2238985

The invention claimed is:

1. A liquid pharmaceutical composition comprising:
   (a) 160 to 250 mg/ml of tocilizumab antibody;
   (b) a histidine buffer;
   (c) 5-15 mM lactic acid or salts thereof;
   (d) arginine;
   (e) a surfactant;
   (f) water for injection; and
   (g) optionally a salt, wherein the composition has a pH between 5.5 and 7.0.

2. The liquid pharmaceutical composition according to claim 1, wherein the composition has a pH between 5.8 and 6.2.

3. The liquid pharmaceutical composition according to claim 1, wherein the composition comprises 5-15 mM sodium lactate.

4. The liquid pharmaceutical composition according to claim 1, wherein the surfactant is a polysorbate.

5. The liquid pharmaceutical composition as claimed in claim 4, wherein the polysorbate is polysorbate 80.

6. The liquid pharmaceutical composition according to claim 1, wherein the optional salt is sodium chloride.

7. The liquid pharmaceutical composition according to claim 1, wherein the composition comprises:
   160 to 200 mg/ml of tocilizumab antibody;
   10 to 25 mM histidine;
   5 to 15 mM sodium lactate or lactic acid;

50 to 150 mM arginine
0.1 to 0.2 mM polysorbate 80
water for injection; and
optionally 5 to 50 mM sodium chloride.

8. A method of manufacturing the liquid pharmaceutical composition of claim 7, comprising mixing together the tocilizumab, the histidine, the sodium lactate or lactic acid, the arginine, the polysorbate 80, and optionally the salt.

9. The liquid pharmaceutical composition according to claim 1, wherein the composition comprises:
160 to 200 mg/ml of tocilizumab antibody;
10 to 25 mM histidine;
5 to 15 mM sodium lactate or lactic acid;
50 to 150 mM arginine
0.1 to 0.2 mM polysorbate 80
water for injection; and
5 to 50 mM sodium chloride.

10. A drug delivery device comprising a liquid pharmaceutical composition as claimed in claim 1.

11. A method of treating rheumatoid arthritis, juvenile idiopathic arthritis, Giant cell arteritis or systemic sclerosis, the method comprising administering to a subject in need thereof a therapeutically effective amount of the
liquid pharmaceutical composition as claimed in claim 1.

12. The liquid pharmaceutical composition according to claim 1, wherein the composition is free of the free amino acid methionine.

13. The liquid pharmaceutical composition according to claim 1, wherein the composition comprises 160-200 mg/ml of tocilizumab antibody.

14. The liquid pharmaceutical composition according to claim 1, wherein the composition comprises 180 mg/ml of tocilizumab antibody.

15. A method of manufacturing the liquid pharmaceutical composition of claim 1, comprising mixing together the tocilizumab, the histidine buffer, the lactic acid or salt thereof, arginine, a surfactant, and optionally the salt.

16. A kit comprising: (i) the liquid pharmaceutical composition of claim 1, and (ii) a drug delivery device; wherein the liquid pharmaceutical composition is optionally contained in a separate package or container from the drug delivery device;
optionally wherein the kit further comprises a set of instructions regarding the administration of the liquid pharmaceutical composition.

17. A method of manufacturing a drug delivery device, comprising incorporating within the device the liquid pharmaceutical composition of claim 1.

18. A liquid pharmaceutical composition comprising:
(a) 160 to 250 mg/ml of tocilizumab antibody;
(b) 10-25 mM histidine buffer;
(c) 5-15 mM lactic acid or salt thereof;
(d) arginine;
(e) a surfactant;
(f) water for injection; and
(g) optionally a salt, wherein the composition has a pH between 5.5 and 7.0.

* * * * *

UNITED STATES PATENT AND TRADEMARK OFFICE
CERTIFICATE OF CORRECTION

PATENT NO. : 11,291,725 B2
APPLICATION NO. : 16/346215
DATED : April 5, 2022
INVENTOR(S) : Jan Jezek et al.

It is certified that error appears in the above-identified patent and that said Letters Patent is hereby corrected as shown below:

In the Claims

In Column 25, Claim 1, Line 55, please replace "mg/mi" with ---mg/ml---

In Column 28, Claim 15, Line 7, please replace "thereof, arginine, a surfactant," with ---thereof, the arginine, the surfactant,---

Signed and Sealed this
Seventeenth Day of May, 2022

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 107
<212> TYPE: PRT
<213> ORGANISM: Artificial sequence
<220> FEATURE:
<223> OTHER INFORMATION: Light chain tocilizumab

```
<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 2
<211> LENGTH: 119
<212> TYPE: PRT
<213> ORGANISM: Artificial sequence
<220> FEATURE:
<223> OTHER INFORMATION: Heavy chain tocilizumab
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
            115
```